US006488656B1

United States Patent
Wu

(12) United States Patent
(10) Patent No.: US 6,488,656 B1
(45) Date of Patent: Dec. 3, 2002

(54) SAFETY SYRINGE

(76) Inventor: Wen-Ying Wu, No. 28, Hsin-Hsing Rd., Chungli City, Taoyuan Hsien (TW)

(*) Notice: Subject to any disclaimer, the term of this patent is extended or adjusted under 35 U.S.C. 154(b) by 0 days.

(21) Appl. No.: 09/863,272

(22) Filed: May 24, 2001

(51) Int. Cl.[7] .................................................. A61M 5/00
(52) U.S. Cl. ...................................... 604/110; 604/197
(58) Field of Search ................................ 604/124, 207, 604/218, 221–222, 228, 110, 181, 186, 187, 192, 197; 128/919

(56) References Cited

U.S. PATENT DOCUMENTS

| | | | | |
|---|---|---|---|---|
| 5,084,017 A | * | 1/1992 | Maffetone | 604/110 |
| 5,125,898 A | * | 6/1992 | Kaufhold et al. | 604/110 |
| 5,383,858 A | * | 1/1995 | Reilly et al. | 604/131 |
| 5,820,605 A | * | 10/1998 | Zdeb et al. | 604/110 |
| 5,899,887 A | * | 5/1999 | Liu | 604/110 |
| 6,196,997 B1 | * | 3/2001 | Saito | 604/110 |

* cited by examiner

*Primary Examiner*—Michael J. Hayes
*Assistant Examiner*—Kathryn L. Assadi
(74) *Attorney, Agent, or Firm*—Fei-Fei Chao; Venable, Baetjer, Howard & Civiletti, LLP

(57) ABSTRACT

A safety syringe has a needle hub detachably mounted at a front end of the barrel and a plunger slidably received in the barrel and having a retaining column extending out from the engaging flange of the plunger. The needle hub has a pair of retaining plates with a slot defined between the retaining plates. The retaining column has a hook and a slanted face, such that when the retaining column is securely clamped by the retaining plates and the needle hub is forced to move inward the barrel, the needle hub is inclined with respect to the barrel.

18 Claims, 9 Drawing Sheets

SAFETY SYRINGE

BACKGROUND OF THE INVENTION

1. Field of the Invention

The present invention relates to a safety syringe, and more particularly to a safety syringe having a plunger with a hook formed on a distal end of the plunger and a needle hub with a pair of retaining plates one of which has an opening defined to correspond to the hook, so that after the hook extends through the opening and securely engages with a periphery of the opening, the needle hub is able to be driven by the plunger into the barrel.

2. Description of Related Art

With reference to FIG. 9, a conventional safety syringe has a needle hub (70) with a bottom (71) defining therein a Y-shaped channel (72) and a plunger (80) with an arrow head (81) formed on a distal end of the plunger (80) to correspond to the Y-shaped channel (72). It is to be noted that the Y-shaped channel (72) is inclined with respect to an imaginary longitudinal axis of the syringe, such that when the arrow head (81) is received in the Y-shaped channel (72) and the plunger (80) is moving away from the needle hub (70), the needle hub (70) will be driven backward into the barrel (82). Because the Y-shaped channel (72) is inclined relative to the imaginary longitudinal axis of the syringe, after the needle hub (70) is completely pulled back in the barrel (82), the needle (73) together with the needle hub (70) is slantedly received in the barrel (82), such that the needle (73) can not be used again. However, when a solution is received in the barrel (82) and the plunger (80) is pushing forward to the needle hub (70), the approaching of the arrow head (81) to the Y-shaped channel (72) stops the flow of the solution out of the needle (73). The pressure of the remaining solution within the barrel (82) also stops the continuous movement of the arrow head (81) to the Y-shaped channel (72), such that the arrow head (81) can not be received in the Y-shaped channel (72) when in application.

To overcome the shortcomings, the present invention tends to provide an improved safety syringe to mitigate and obviate the aforementioned problems.

SUMMARY OF THE INVENTION

The primary objective of the present invention is to provide a safety syringe having a plunger with a head integrally formed on a distal end of the plunger by means of a neck, wherein the head has a hook formed on a sidewall of the head and a slanted face formed oppositely to the hook and a needle hub with a pair of retaining plates one of which has an opening defined to correspond to the hook and a slit defined between the two retaining plates. When the hook is approaching the opening, the remaining solution inside the barrel can still flow through the slit and out of the needle.

Another objective of the present invention is to provide a positioning device to secure the alignment of the hook to the opening during the movement of the plunger, so that a user will not have to rotate the plunger to align the hook to the opening after use.

Other objects, advantages and novel features of the invention will become more apparent from the following detailed description when taken in conjunction with the accompanying drawings.

DETAILED DESCRIPTION OF PREFERRED EMBODIMENT

Figure 1:
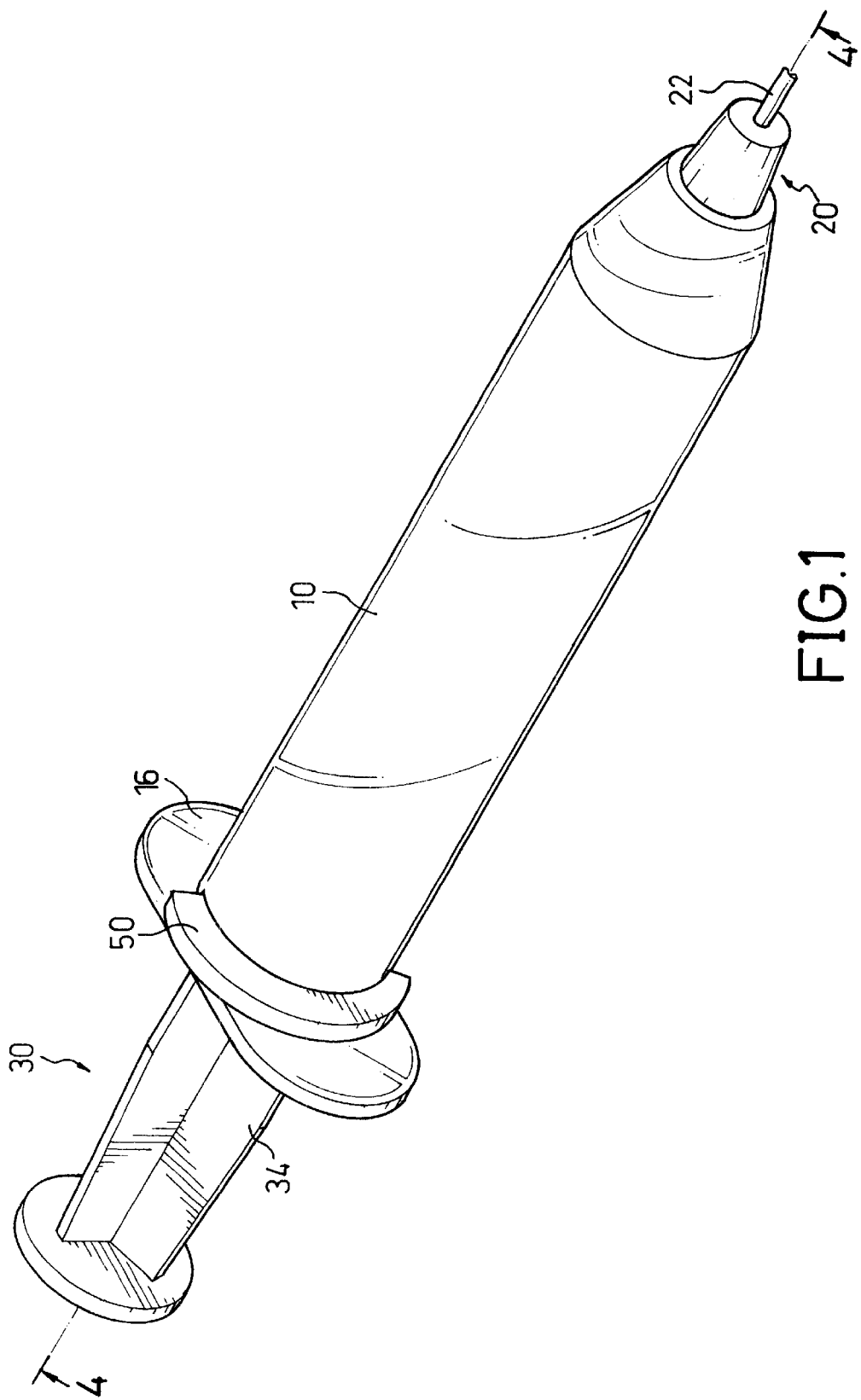
FIG. 1 is a perspective view of the safety syringe of the present invention.

With reference to FIG. 1, a safety syringe in accordance with the present invention has a barrel (10), a needle hub (20) and a plunger (30).

Figure 2:
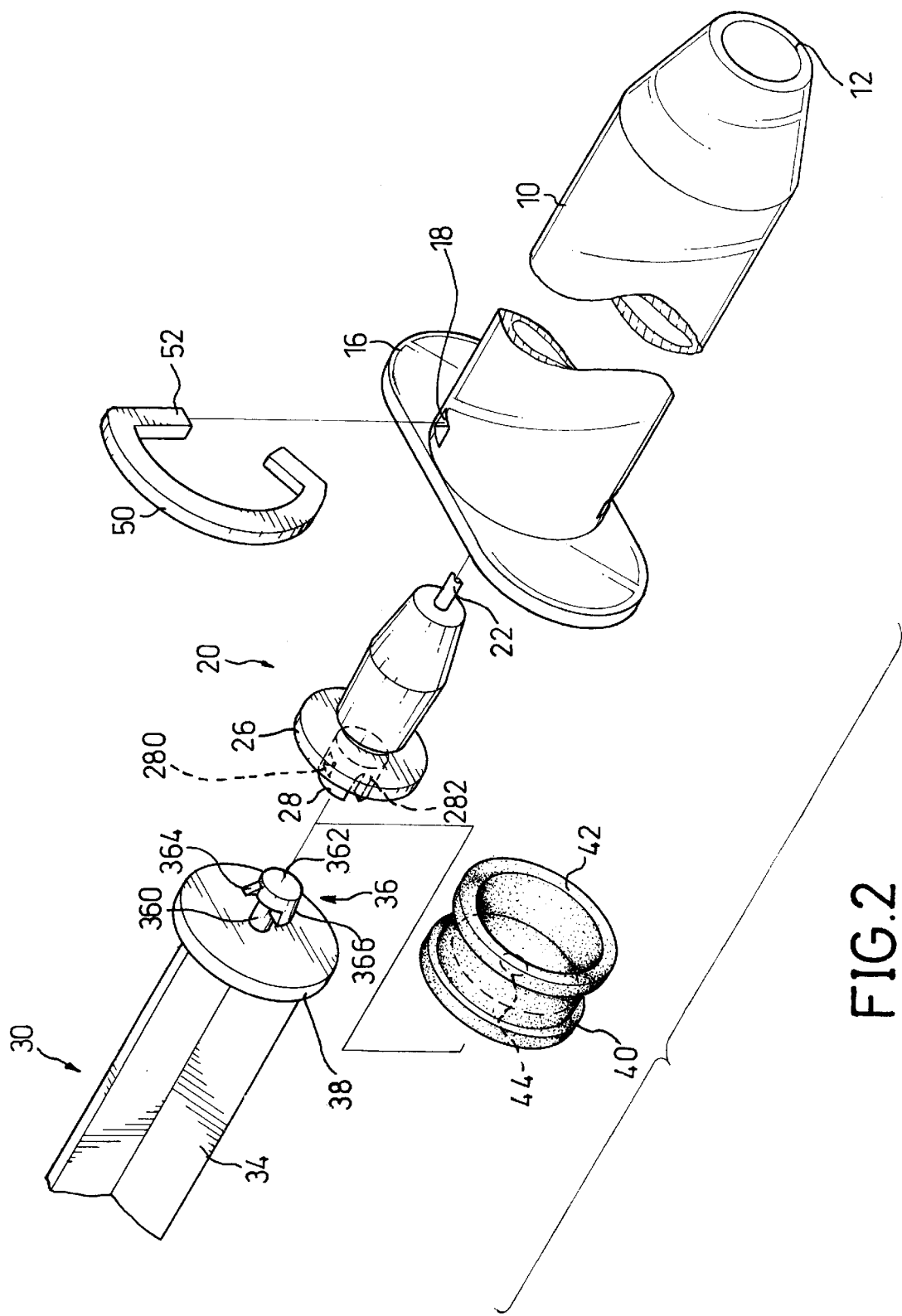
FIG. 2 is an exploded perspective view of the safety syringe of FIG. 1.

With reference to FIG. 2 and still taking FIG. 1 for reference, the barrel (10) has a through hole (12) defined in a front end of the barrel (10), a finger flange (16) formed on a rear end and around an outer periphery of the barrel (10) and a pair of apertures (18) defined in the outer periphery of the barrel (10). The needle hub (20) has a needle (22), a flange (26) and a pair of retaining plates (28). The needle (22) is securely engaged with the needle hub (20) and extends out of the needle hub (20). The flange (26) is integrally formed on a distal end of the needle hub (20) opposite to the needle (22). One of the retaining plates (28) has an opening (280) defined in a side face of the retaining plate (28) and a slot (282) is defined between the two retaining plates (28). The plunger (30) has ribs (34) axially extending from an engaging flange (38). A retaining column (36) extends oppositely to the ribs (34) by a neck (360) bridging between the engaging flange (38) and the retaining column (36). The column (36) has a head (362) having a diameter larger than the diameter of the neck (360) and a hook (364) formed on a sidewall of the head (362). The head (362) further has a slanted sidewall (366) oppositely formed to the hook (364). A rubber-made seal (40) has a closed end with a hole (44) and an open end defining therein a space (42). The hole (44) is defined to correspond to the retaining column (36) such that the retaining column (36) is able to extend through the hole (44) and the seal (40) is retained between the head (362) and the engaging flange (38), as shown in FIG. 2. Furthermore, a guiding device (50) has two guiding points (52) extending toward each other. The positioning points (52) correspond to the apertures (18) in the outer periphery of the barrel (10).

Figure 3:
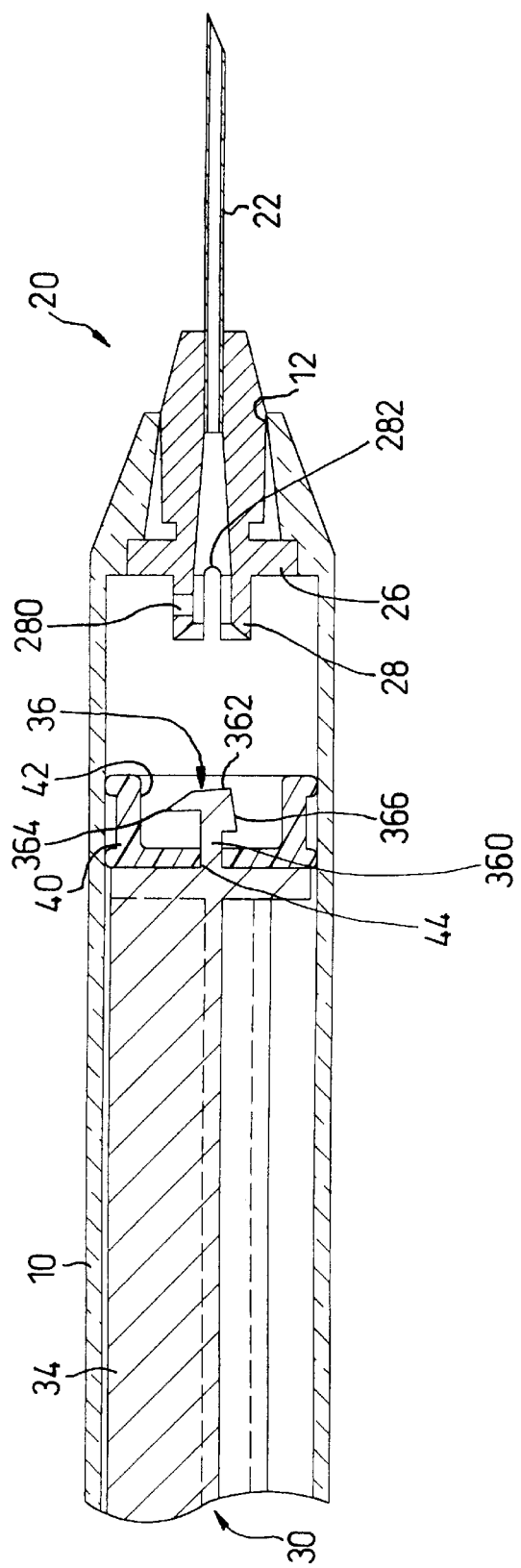
FIG. 3 is a cross sectional view showing a status before the engagement of the hook and the opening of the retaining plate.

With reference to FIG. 3, when the syringe of the present invention is assembled, as previously described, the seal (40) is received between the engaging flange (38) and the head (362) with the head (362) together with the hook (364) extending through the hole (44) of the seal (40). The needle hub (20) is detachably engaged with the barrel (10) with the needle (22) extending through the through hole (12) of the barrel (10).

Figure 4:
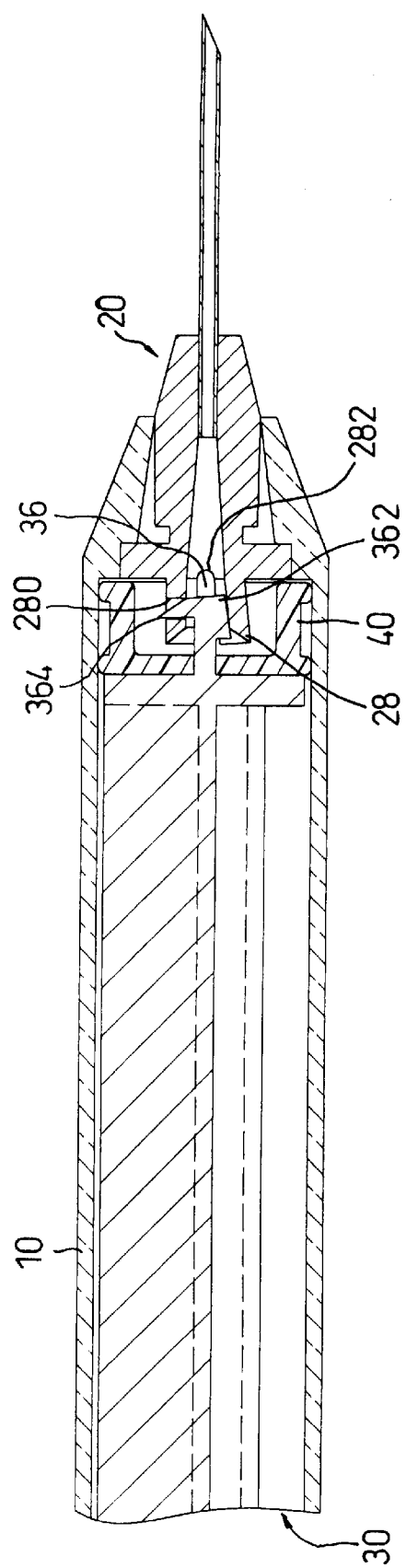
FIG. 4 is a cross sectional view taken along the line 4—4 of FIG. 1, wherein the hook is received in the opening of the retaining plate.

With reference to FIG. 4, when a solution is received in the barrel (10) and the plunger (30) is pushed toward the needle hub (20), the solution inside the barrel (10) is able to flow through the slot (282) between the two retaining plates (28) and into the needle (22) even after the head (362) extends between the two retaining plates (28) with the hook (364) extending outward from the opening (280) of the retaining plate (28).

Figure 5:
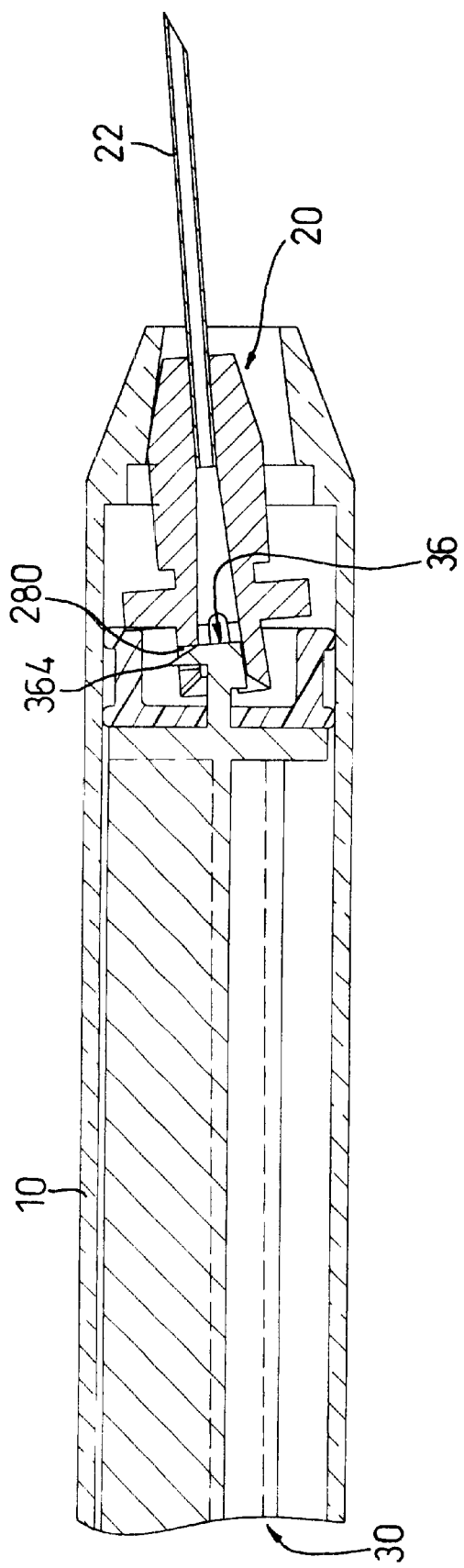
FIG. 5 is a schematic cross sectional view of the initial disengagement of th needle hub to the front end of the barrel.
Figure 6:
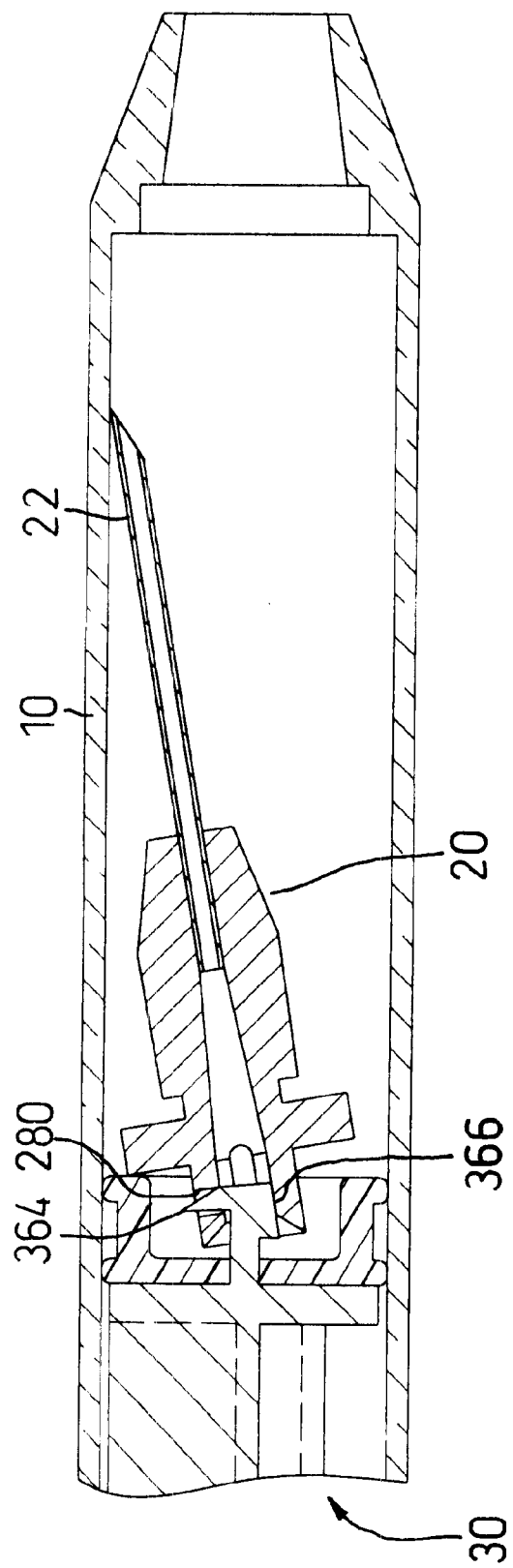
FIG. 6 is a schematic cross sectional view showing that the needle hub is completely disengaged from the front end of the barrel.
Figure 7:
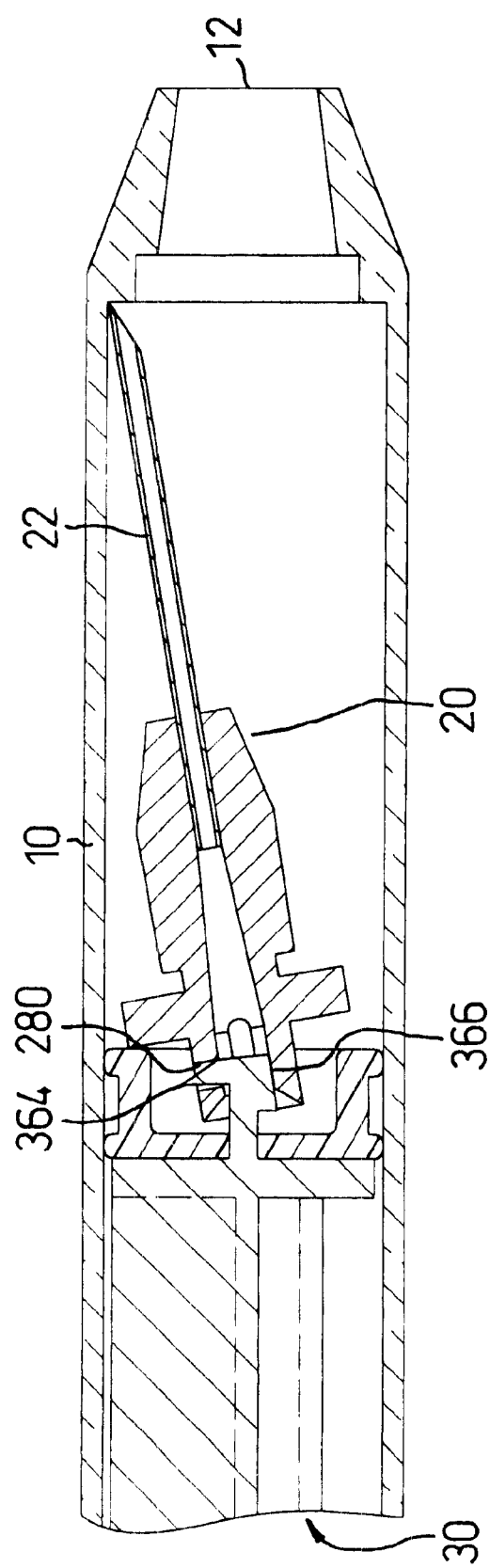
FIG. 7 is a schematic cross sectional view showing the abutment of the needle to an inner face of the barrel.

With reference to FIGS. 5, 6 and 7, after the hook (364) is received in the opening (280) of one of the retaining plates (28), because the diameter of the head (362) is larger than the diameter of the slot (282) between the two retaining plates (28), the head (362) will force the retaining plates (28) to expand thereby allowing one of the retaining plates (28) to securely abut the slanted face (366) of the head (362). Accordingly, after the needle hub (20) is pulled backward into the barrel (10), the abutment of the retaining plate (28) to the slanted face (366) of the head (362) causes the needle hub (20) to incline relative to the barrel (10) after the disengagement of the needle hub (20) with the front end of the barrel (10). Thereafter when the plunger (30) pushes the needle hub (20) toward the front end of the barrel (10) again, due to the inclination of the needle hub (20), the front end of the needle (22) will abut an inner face of the barrel (10). Thus, safety of after using the syringe is accomplished.

Figure 8:
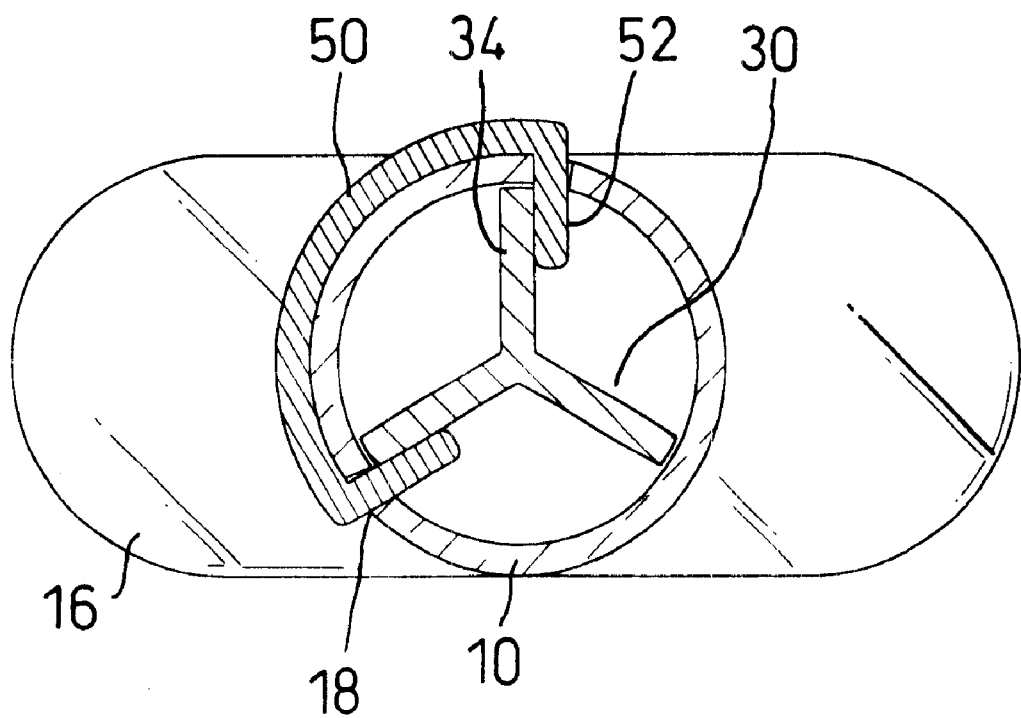
FIG. 8 is a cross sectional view taken from the line 8—8 of FIG. 1.
Figure 9:
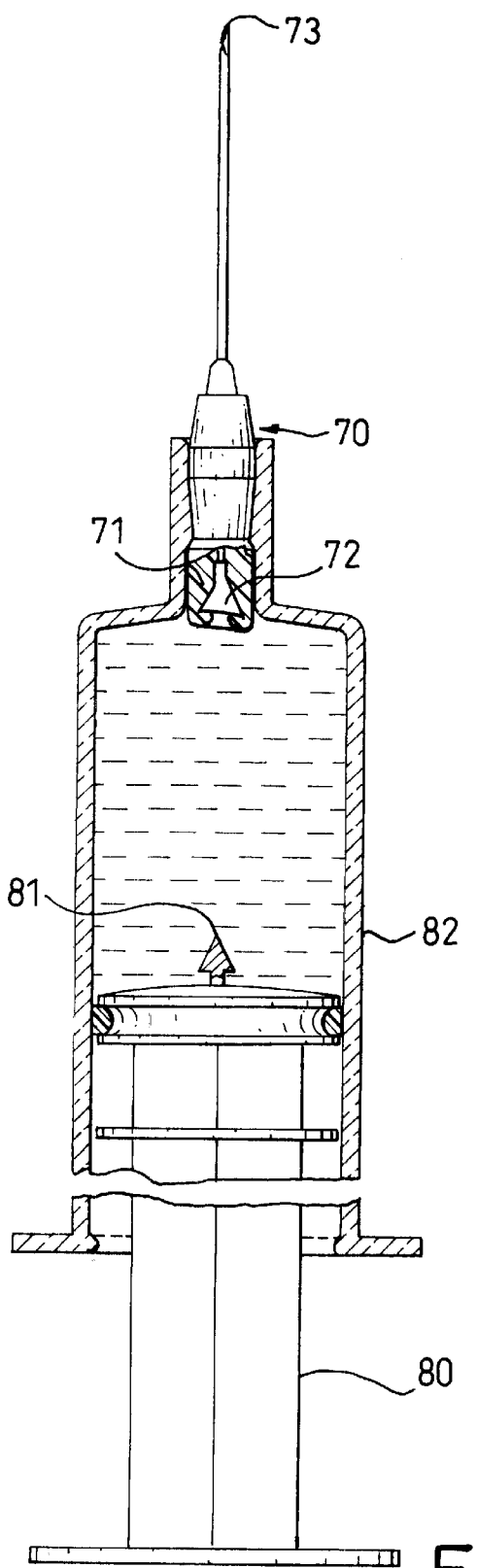
FIG. 9 is a cross sectional view showing a conventional syringe.

Furthermore, with reference to FIG. 8, in order to have the alignment between the hook (364) and the opening (280), the guiding device (50) is mounted on the outer periphery of the barrel (10) with the guiding points (52) received in the corresponding apertures (18) of the barrel (10). After the extension of the guiding points (52) into the apertures (118), the guiding points (52) are slidably engaged with two of the ribs (34), which guides the movement of the plunger (30) inside the barrel (10) to ensure the alignment of the hook (364) to the opening (280). Naturally, a user may still use this syringe without the guiding device (50). The user may rotate the plunger (30) inside the barrel (10) to align the hook (364) to the opening (280) after injection.

It is concluded that the syringe of the present invention has the advantages such as:

Easy pushing of the plunger;

Because the solution inside the barrel (10) is able to flow through the slot (282) even after the head (362) is received between the pair of retaining plates (28), the plunger (30) has no resistance to approach the needle hub (20).

Accurate alignment between the hook (364) and the opening (280);

With the limitation of the guiding points (52) of the guiding device (50), the movement and potential rotation of the plunger (30) are guided.

Ensured safety;

Due to the slanted face (366) on the head (362), the needle hub (20) is inclined when pulled backward into the barrel (10), such that a reuse of the needle hub (20) together with the needle (22) is prevented.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising:
    a barrel with a through hole defined in a front end of the barrel;
    a needle hub detachably engaged with the barrel and having a needle securely engaged at a front end of the needle hub, a flange formed on a rear end of the needle hub and around an outer periphery of the needle hub and a pair of retaining plates extending from the rear end of the needle hub and provided with a slot defined between the pair of retaining plates, wherein one of the pair of retaining plates defines therein an opening;
    a plunger slidably received in the barrel and having ribs axially extending in a longitudinal axis of the plunger, an engaging flange formed at a front end of the plunger and a retaining column extending out from the engaging flange to be detachably received between the pair of retaining plates, the retaining column having a hook formed to correspond to the opening of one of the retaining plates and a slanted face oppositely formed to the hook, whereby when the hook is received in the opening of one of the retaining plates and the needle hub is forced to move into the barrel, the needle hub will be inclined with respect to the barrel; and
    a seal securely mounted around the retaining column so as to ensure a water tight engagement between the plunger and the barrel.

2. The safety syringe as claimed in claim 1, wherein the retaining column has a diameter larger than a diameter of the retaining plates so as that when the retaining column is received between the retaining plates, the retaining column is able to be securely clamped by the retaining plates.

3. The safety syringe as claimed in claim 1, wherein the retaining column comprises a neck extending out from the engaging flange and a head formed on a free end of the neck and wherein the hook and the slanted face are formed on the head.

4. The safety syringe as claimed in claim 2, wherein the retaining column comprises a neck extending out from the engaging flange and a head formed on a free end of the neck and wherein the hook and the slanted face are formed on the head.

5. The safety syringe as claimed in claim 1 further comprising a guiding device detachably mounted on the barrel to limit the rotation of the plunger inside the barrel.

6. The safety syringe as claimed in claim 2 further comprising a guiding device detachably mounted on the barrel to limit the rotation of the plunger inside the barrel.

7. The safety syringe as claimed in claim 3 further comprising a guiding device detachably mounted on the barrel to limit the rotation of the plunger inside the barrel.

8. The safety syringe as claimed in claim 4 further comprising a guiding device detachably mounted on the barrel to limit the rotation of the plunger inside the barrel.

9. The safety syringe as claimed in claim 5, wherein the guiding device has two guiding points each extending through the barrel to slidably engage with one of the ribs such that rotation of the plunger inside the barrel is prevented.

10. The safety syringe as claimed in claim 6, wherein the guiding device has two guiding points each extending through the barrel to slidably engage with one of the ribs such that rotation of the plunger inside the barrel is prevented.

11. The safety syringe as claimed in claim 7, wherein the guiding device has two guiding points each extending through the barrel to slidably engage with one of the ribs such that rotation of the plunger inside the barrel is prevented.

12. The safety syringe as claimed in claim 8, wherein the guiding device has two guiding points each extending through the barrel to slidably engage with one of the ribs such that rotation of the plunger inside the barrel is prevented.

13. The safety syringe as claimed in claim 3, wherein the seal is received between the engaging flange and the head and has a space defined to receive therein the head.

14. The safety syringe as claimed in claim 5, wherein the seal is received between the engaging flange and the head and has a space defined to receive therein the head.

15. The safety syringe as claimed in claim 9, wherein the seal is received between the engaging flange and the head and has a space defined to receive therein the head.

16. The safety syringe as claimed in claim 13, wherein the seal has a hole defined in a bottom of the seal to allow the extension of the head.

17. The safety syringe as claimed in claim 14, wherein the seal has a hole defined in a bottom of the seal to allow the extension of the head.

18. The safety syringe as claimed in claim 15, wherein the seal has a hole defined in a bottom of the seal to allow the extension of the head.

* * * * *